US 6,725,490 B2

(12) United States Patent
Blaustein et al.

(10) Patent No.: US 6,725,490 B2
(45) Date of Patent: Apr. 27, 2004

(54) COMPLEX MOTION TOOTHBRUSH

(75) Inventors: Lawrence A. Blaustein, Moreland Hills, OH (US); Douglas A. Gall, Westlake, OH (US); Patrick W. Brown, Mantua, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 134 days.

(21) Appl. No.: 09/993,167

(22) Filed: Nov. 6, 2001

(65) Prior Publication Data
US 2003/0084524 A1 May 8, 2003

(51) Int. Cl.[7] .............................. A61C 17/34
(52) U.S. Cl. ............... 15/22.2; 15/22.1; 15/28
(58) Field of Search ............. 15/22.1, 22.2, 15/22.4, 28

(56) References Cited

U.S. PATENT DOCUMENTS

| | | | |
|---|---|---|---|
| 1,212,001 A | 1/1917 | Baxter | 15/22.4 |
| 1,255,028 A | 1/1918 | Leonard et al. | 601/89 |
| 2,140,307 A | 12/1938 | Belaschk et al. | 15/28 |
| 2,215,031 A | 9/1940 | Elmore | 15/28 |
| 2,379,049 A | 6/1945 | Tompkins | 15/22.1 |
| 2,682,066 A | 6/1954 | Keely | 15/22.1 |
| 2,799,878 A | 7/1957 | Brausch | 15/22.1 |
| 3,103,027 A | 9/1963 | Birch | 15/110 |
| 3,129,449 A | 4/1964 | Cyzer | 15/28 |
| 3,230,562 A | 1/1966 | Birch | 15/110 |
| 3,242,516 A | 3/1966 | Cantor | 15/28 |
| 3,284,829 A | 11/1966 | Allen | 15/22.1 |
| 3,577,579 A | 5/1971 | Duve | 15/22.1 |
| 4,081,876 A | 4/1978 | Pugh | 15/167.1 |
| 4,131,967 A | 1/1979 | Northemann et al. | 15/167.2 |
| 4,156,620 A | 5/1979 | Clemens | 134/6 |
| 4,181,997 A | 1/1980 | O'Rourke | 15/24 |
| 4,274,173 A | 6/1981 | Cohen | 15/28 |
| 4,479,516 A | 10/1984 | Hunter | 15/22.1 |
| 4,545,087 A | 10/1985 | Nahum | 15/22.1 |
| 4,603,448 A | 8/1986 | Middleton et al. | 15/22.1 |
| 4,766,630 A | 8/1988 | Hegemann | 15/21.1 |
| 4,795,347 A | 1/1989 | Maurer | 433/216 |
| 4,827,550 A | 5/1989 | Graham et al. | 15/22.1 |
| 4,845,795 A | 7/1989 | Crawford et al. | 15/22.1 |
| 4,894,880 A | 1/1990 | Aznavoorian | 15/167.2 |
| 4,989,287 A | 2/1991 | Scherer | 15/22.1 |

(List continued on next page.)

FOREIGN PATENT DOCUMENTS

| | | |
|---|---|---|
| AU | 643917 | 5/1990 |
| AU | 690732 | 8/1995 |
| AU | 200128902 | 1/2001 |

(List continued on next page.)

OTHER PUBLICATIONS

PUB Bader, Review of Currently Available Battery–Operated Toothbrushes, Compend. Conti. Educ. Dent., vol. XIII, No. 12, p. 1162, 1164–69.
Photographs of electric toothbrush of BioBrush Industries (22 photographs).
English Translation of Taiwan Patent Document TW 135303, Jun. 1990.

*Primary Examiner*—Mark Spisich
(74) *Attorney, Agent, or Firm*—James C. Vago

(57) ABSTRACT

An electrically driven toothbrush has a rotatable shaft with a cam preferably at a remote end of the shaft, which fits into a slot in a bristle holder. The holder is mounted for rotation in a toothbrush head. When the shaft rotates cam describes a circle and drivingly engages the slot to cause the holder to vibrate in a first brushing motion. A second bristle holder is also driven by the shaft, for a second kind of brushing motion. The second bristle holder is driven through and engagement with a portion of the remote end and/or with one or more additional cams or cam portions included on the shaft.

43 Claims, 8 Drawing Sheets

U.S. PATENT DOCUMENTS

| | | | |
|---|---|---|---|
| 5,046,213 A | 9/1991 | Curtis et al. | 15/167.1 |
| D321,285 S | 11/1991 | Hirabayashi | D4/101 |
| 5,068,939 A | 12/1991 | Holland | 15/22.1 |
| 5,070,567 A | 12/1991 | Holland | 15/28 |
| 5,077,855 A | 1/1992 | Ambasz | 15/22.1 |
| 5,088,145 A | 2/1992 | Whitefield | 15/22.1 |
| 5,099,536 A | 3/1992 | Hirabayashi | 15/28 |
| 5,138,734 A | 8/1992 | Chung | 15/28 |
| 5,142,723 A | 9/1992 | Lustig et al. | 15/22.1 |
| 5,145,369 A | 9/1992 | Lustig et al. | 433/118 |
| D330,286 S | 10/1992 | Curtis et al. | D4/104 |
| 5,170,525 A | 12/1992 | Cafaro | 15/28 |
| 5,177,826 A | 1/1993 | Vrignaud et al. | 15/22.1 |
| 5,186,627 A | 2/1993 | Amit et al. | 433/216 |
| D334,473 S | 4/1993 | Volpenhein et al. | D4/104 |
| 5,226,206 A | 7/1993 | Davidovitz et al. | 15/22.1 |
| 5,259,083 A * | 11/1993 | Stansbury, Jr. | 15/22.1 |
| 5,276,932 A | 1/1994 | Byrd | 15/28 |
| 5,284,168 A | 2/1994 | Klinkhammer | 132/308 |
| 5,335,389 A | 8/1994 | Curtis et al. | 15/167.1 |
| 5,353,460 A | 10/1994 | Bauman | 15/22.1 |
| 5,359,747 A | 11/1994 | Amakasu | 15/22.1 |
| 5,360,025 A | 11/1994 | Klinkhammer | 132/308 |
| 5,360,026 A | 11/1994 | Klinkhammer | 132/308 |
| 5,392,483 A | 2/1995 | Heinzelman et al. | 15/167.1 |
| 5,404,608 A | 4/1995 | Hommann | 15/22.1 |
| 5,416,942 A * | 5/1995 | Baldacci et al. | 15/22.1 |
| 5,435,032 A | 7/1995 | McDougall | 15/22.1 |
| 5,435,034 A | 7/1995 | Bigler et al. | 15/22.1 |
| 5,442,827 A | 8/1995 | Hommann | 15/22.1 |
| 5,446,940 A | 9/1995 | Curtis et al. | 15/167.1 |
| 5,500,970 A | 3/1996 | Maurer et al. | 15/22.1 |
| 5,504,958 A | 4/1996 | Herzog | 15/22.1 |
| 5,504,960 A | 4/1996 | Hommann | 15/22.1 |
| 5,507,959 A | 4/1996 | Glick | 15/22.1 |
| 5,524,312 A | 6/1996 | Tan et al. | 15/22.1 |
| 5,617,601 A | 4/1997 | McDougall | 15/22.1 |
| 5,617,603 A * | 4/1997 | Mei | 15/22.1 |
| 5,625,916 A | 5/1997 | McDougall | 15/28 |
| 5,715,556 A | 2/1998 | Chung | 15/22.1 |
| 5,727,273 A | 3/1998 | Pai | 15/22.1 |
| 5,732,432 A | 3/1998 | Hui | 15/22.1 |
| 5,732,433 A * | 3/1998 | Gocking et al. | 15/28 |
| 5,735,011 A | 4/1998 | Asher | 15/167.1 |
| 5,778,474 A * | 7/1998 | Shek | 15/22.1 |
| 5,784,743 A | 7/1998 | Shek | 15/22.1 |
| D397,252 S | 8/1998 | Allende | D4/101 |
| 5,802,656 A | 9/1998 | Dawson et al. | 15/110 |
| 5,836,030 A | 11/1998 | Hazeu et al. | 15/22.1 |
| 5,842,244 A | 12/1998 | Hilfinger et al. | 15/22.1 |
| 5,842,245 A | 12/1998 | Pai | 15/22.1 |
| 5,842,249 A | 12/1998 | Sato | 15/167.2 |
| 5,850,655 A | 12/1998 | Göcking et al. | 15/28 |
| 5,876,206 A | 3/1999 | Maurer | 433/216 |
| 5,901,397 A | 5/1999 | Hafele et al. | 15/22.1 |
| 5,996,157 A | 12/1999 | Smith et al. | 15/28 |
| 6,000,083 A | 12/1999 | Blaustein et al. | 15/28 |
| 6,006,394 A | 12/1999 | Bredall et al. | 15/167.1 |
| 6,032,313 A | 3/2000 | Tsang | 15/22.1 |
| 6,106,290 A | 8/2000 | Weissman | 433/122 |
| D432,312 S | 10/2000 | Blaustein et al. | D4/104 |
| 6,138,310 A | 10/2000 | Porper et al. | 15/22.2 |
| D433,814 S | 11/2000 | Blaustein et al. | D4/104 |
| D434,563 S | 12/2000 | Lim et al. | D4/104 |
| 6,178,579 B1 | 1/2001 | Blaustein et al. | 15/28 |
| 6,189,693 B1 | 2/2001 | Blaustein et al. | 206/362.2 |
| 6,209,164 B1 | 4/2001 | Sato | 15/167.2 |
| 6,237,178 B1 | 5/2001 | Krammer et al. | 15/22.1 |
| 6,308,358 B2 | 10/2001 | Gruber et al. | 15/22.1 |
| 6,311,837 B1 | 11/2001 | Blaustein et al. | 206/362.2 |
| 6,349,442 B1 | 2/2002 | Cohen et al. | 15/22.1 |
| 6,360,395 B2 | 3/2002 | Blaustein et al. | 15/28 |
| 6,371,294 B1 | 4/2002 | Blaustein et al. | 206/362.2 |
| D456,998 S | 5/2002 | Blaustein et al. | D4/101 |
| D457,728 S | 5/2002 | Blaustein et al. | D4/104 |
| D458,030 S | 6/2002 | Blaustein et al. | D4/104 |
| D458,455 S | 6/2002 | Blaustein et al. | D4/104 |
| D459,894 S | 7/2002 | Blaustein et al. | D4/107 |
| D459,895 S | 7/2002 | Blaustein et al. | D4/107 |
| 6,421,865 B1 | 7/2002 | McDougall | 15/22.1 |
| 6,421,866 B1 | 7/2002 | McDougall | 15/22.1 |
| D461,642 S | 8/2002 | Blaustein et al. | D4/107 |
| 6,434,773 B1 * | 8/2002 | Kuo | 15/22.1 |
| D465,088 S | 11/2002 | Blaustein et al. | D4/101 |
| 6,574,820 B1 | 6/2003 | DePuydt et al. | 15/28 |
| 2001/0001334 A1 | 5/2001 | Gruber et al. | 15/22.1 |
| 2001/0004781 A1 | 6/2001 | Blaustein et al. | 15/28 |
| 2001/0020314 A1 | 9/2001 | Calabrese | 15/22.1 |
| 2001/0022277 A1 | 9/2001 | Blaustein et al. | 206/362.2 |
| 2001/0054561 A1 | 12/2001 | Blaustein et al. | 206/362.2 |
| 2002/0017474 A1 | 2/2002 | Blaustein et al. | 206/362.2 |
| 2002/0020645 A1 | 2/2002 | Blaustein et al. | 206/362.2 |
| 2002/0029988 A1 | 3/2002 | Blaustein et al. | 206/362.2 |
| 2002/0032941 A1 | 3/2002 | Blaustein et a. | 15/22.1 |
| 2002/0038772 A1 | 4/2002 | Blaustein et al. | 206/362.2 |
| 2002/0078514 A1 | 6/2002 | Blaustein et al. | 15/22.1 |
| 2002/0152564 A1 | 10/2002 | Blaustein et al. | 15/22.1 |
| 2002/0162180 A1 | 11/2002 | Blaustein et al. | 15/22.1 |

FOREIGN PATENT DOCUMENTS

| | | |
|---|---|---|
| CA | 1082408 | 7/1980 |
| CA | 2141569 | 2/2000 |
| CN | 1105173 | 7/1995 |
| CN | 2236827 Y | 10/1996 |
| CN | 2271352 Y | 12/1997 |
| CN | 2271353 Y | 12/1997 |
| CN | 2274947 | 2/1998 |
| CN | 97325183.2 | 12/1998 |
| CN | 2324988 Y | 6/1999 |
| DE | 2654853 | 6/1978 |
| DE | 2736286 | 7/1978 |
| DE | 8426426.8 | 3/1985 |
| DE | 3406112 | 8/1985 |
| DE | 4441571 | 12/1995 |
| DE | 29600236 | 4/1996 |
| DE | 29600255 | 5/1996 |
| DE | 29613608 | 11/1996 |
| DE | 29618755 | 3/1997 |
| DE | 29517610 | 4/1997 |
| DE | 29701302 | 8/1997 |
| DE | 29809977 | 2/1999 |
| DE | 19803311 | 8/1999 |
| EP | 0098275 | 11/1985 |
| EP | 254397 | 1/1988 |
| EP | 0259648 | 3/1988 |
| EP | 0374152 | 8/1988 |
| EP | 208401 | 5/1991 |
| EP | 520985 | 1/1993 |
| EP | 0537465 | 4/1993 |
| EP | 546203 | 6/1993 |
| EP | 0569606 | 11/1993 |
| EP | 0689404 | 1/1996 |
| EP | 1053721 | 11/2000 |
| FR | 1121618 | 8/1956 |
| GB | 452961 | 9/1936 |
| GB | 989953 | 4/1965 |
| GB | 1008530 | 10/1965 |
| GB | 1583558 | 1/1981 |
| GB | 2237505 | 5/1991 |
| GB | 2290224 | 12/1995 |
| GB | 2319170 | 5/1998 |

| | | | | | | |
|---|---|---|---|---|---|---|
| GB | 3004958 | 7/2002 | | TW | 253174 | 8/1995 |
| JP | 3001895 | 6/1905 | | TW | 311444 | 12/1996 |
| JP | 57-89810 | 6/1982 | | TW | 330410 | 12/1996 |
| JP | 63-168108 | 7/1988 | | TW | 309753 | 7/1997 |
| JP | 2-19241 | 2/1990 | | TW | 330411 | 4/1998 |
| JP | 4-133733 | 7/1991 | | TW | 406557 | 5/1998 |
| JP | 5-146314 | 6/1993 | | TW | 334345 | 6/1998 |
| JP | 5-269023 | 10/1993 | | TW | 339233 | 8/1998 |
| JP | 6-047298 | 2/1994 | | TW | 455298 | 9/2001 |
| JP | 6-189822 | 7/1994 | | TW | 455299 | 9/2001 |
| JP | 7-116023 | 5/1995 | | WO | 83/03956 | 11/1983 |
| JP | 7-116024 | 5/1995 | | WO | 91/13570 | 9/1991 |
| JP | 2511226 | 7/1996 | | WO | 92/19177 | 11/1992 |
| JP | 507030 | 7/1997 | | WO | 93/20777 | 10/1993 |
| JP | 10-66704 | 3/1998 | | WO | 94/09676 | 5/1994 |
| JP | 10-507375 | 7/1998 | | WO | 94/21191 | 9/1994 |
| JP | 2811246 | 8/1998 | | WO | 95/11636 | 5/1995 |
| KR | 1986-0001137 | 6/1986 | | WO | 95/27419 | 10/1995 |
| KR | 1991-700015 | 3/1991 | | WO | 97/20484 | 6/1997 |
| KR | 1999-0028614 | 3/2000 | | WO | 97/25899 | 7/1997 |
| TW | 257968 | 6/1905 | | WO | 97/34545 | 9/1997 |
| TW | 96609 | 6/1976 | | WO | 98/26729 | 6/1998 |
| TW | 154730 | 3/1979 | | WO | 98/26730 | 6/1998 |
| TW | 164493 | 7/1979 | | WO | 99/12492 | 3/1999 |
| TW | 200663 | 5/1981 | | WO | 99/23910 | 5/1999 |
| TW | 229411 | 5/1982 | | WO | 99/37180 | 7/1999 |
| TW | 228087 | 11/1983 | | WO | 99/56660 | 11/1999 |
| TW | 274724 | 4/1984 | | WO | 00/56186 | 9/2000 |
| TW | 135303 | 6/1990 | | WO | 00/78244 | 12/2000 |
| TW | 137856 | 7/1990 | | WO | 01/32095 | 5/2001 |
| TW | 212909 | 9/1993 | | WO | 01/52696 | 7/2001 |
| TW | 294031 | 11/1994 | | | | |
| TW | 239963 | 2/1995 | | * cited by examiner | | |
| TW | 239964 | 2/1995 | | | | |

COMPLEX MOTION TOOTHBRUSH

BACKGROUND OF THE INVENTION

1. Field of the Invention

The invention is related to the art of toothbrushes.

2. Description of Related Art

The invention relates more particularly to electrically driven toothbrushes in which brush bristles are arranged to be moved relative to the toothbrush handle. There are many examples of such toothbrushes including the disclosure in 1939 of rotary driven bristles in U.S. Pat. No. 2,215,031, A similar rotational drive arrangement is also shown in U.S. Pat. No. 4,845,795, U.S. Pat. No. 4,156,620 explains how a rotational motor drive is converted into reciprocal linear motion to drive the bristles rotationally clockwise and counterclockwise, U.S. Pat. No. 3,577,579 discloses a toothbrush in which a toothbrush head is moved in relation to a brush holder so that all the bristles mounted in the brush head move together sideways and backwards and forwards relative to the holder. U.S. Pat. No. 5,625,916, the substance of which is hereby incorporated by reference, discloses a toothbrush with a single bristle holder. The bristle holder is driven to vibrate in a rotational manner about a shaft.

The drive mechanisms and brush motions disclosed in these references range from the relatively simple to the relatively complex. The most complex of the disclosed toothbrushes is used to provide an elaborate brushing motion. While the provided brushing motion is beneficial, the means disclosed for providing it is far too complicated and involves far too many moving parts, to be a practical brushing solution in many applications. The simpler of the disclosed toothbrushes, provide only one brushing action. While practical to produce, these single brushing actions may be inadequate in some brushing applications. For example, they may not adequately clean spaces between teeth.

It is desirable therefore, to provide a toothbrush that is simple to manufacture, and has few moving parts, while providing a plurality of cleaning or brushing actions for accomplishing a plurality of teeth cleaning tasks.

BRIEF SUMMARY OF THE INVENTION

One embodiment of the new toothbrush includes a handle at a first end of the toothbrush, a head at a second end of the toothbrush, a rotatable shaft extending from the handle to the head and having a first longitudinal central axis, a first bristle holder pivotally mounted to the head and associated with a remote end of the shaft, the remote end of the shaft being received in a slot of the first bristle holder for driving the first bristle holder in pivoting vibratory movement, and a second bristle holder movably mounted to the head section and drivingly engaged by a cam located on the shaft.

Another embodiment of the electric toothbrush includes a shaft. The shaft includes a first cam and a second cam. A motor operative to rotate the shaft is also included in the toothbrush. A first brush section is operatively coupled to the first cam for a first motion. A second brush section longitudinally separated from the first brush section and separately associated with the second cam to drive the second brush section in a second motion. The second motion being distinct from the first motion.

A third embodiment of the electric toothbrush includes a shaft. The shaft includes a cam. A motor is operative to rotate the shaft. A first brush section is operatively coupled to the cam for a first motion. A second brush section is longitudinally separated from the first brush section and separately operatively coupled to the cam for a second motion. The second motion is distinct from the first motion.

For example, the second brush section can include a pivot portion located in a body of the second brush section and disposed transversely to a longitudinal axis of the second brush section, the pivot portion being operative to pivotably connect the second brush section to a head portion of the toothbrush. The second brush section includes a cam contact surface on a bottom surface thereof. The cam contact surface is operative to ride on a surface of the cam, thereby causing the second brush section to rock about the pivot portion.

One advantage of the present invention resides in distinct and complementary cleaning motions provided respectively by the first and second bristle holders Another advantage of the present invention is that distinct and complementary cleaning motions are provided in a simple and economical toothbrush.

Still other advantages of the present invention will become apparent to those skilled in the art upon a reading and understanding of the detail description below.

BRIEF DESCRIPTION OF THE SEVERAL VIEWS OF THE DRAWINGS

The invention may take form in various components and arrangements of components, and in various procedures and arrangements of procedures. The drawings are only for purposes of illustrating preferred embodiments, they are not to scale, and are not to be construed as limiting the invention.

DETAILED DESCRIPTION OF THE INVENTION

Figure 1:
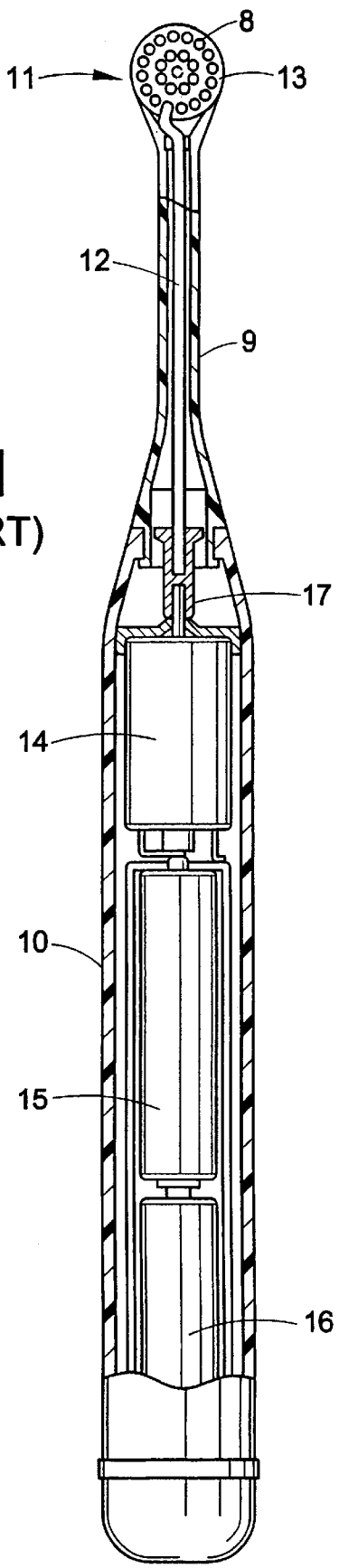
FIG. 1 is a sectional bottom view of a toothbrush.
Figure 4:
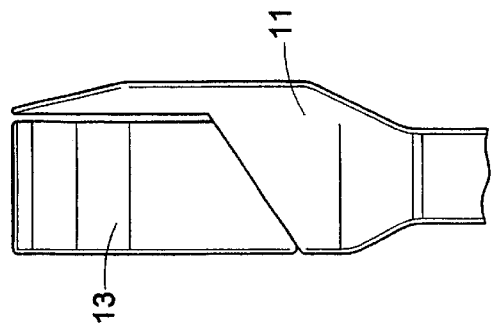
FIG. 4 is an opposite side view of FIG. 2.
Figure 7:
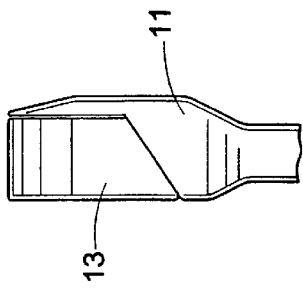
FIGS. 5, 6 and 7 are respectively the same views as FIGS. 2, 3 and 4 of a different toothbrush and to a different scale.

Referring to the drawings, in FIG. 1 the toothbrush comprises a handle 10 at a first end of the toothbrush, a head 11 at a second end of the toothbrush, a neck 9 extending therebetween, a rotatable shaft 12 extending from the handle to the head, and a generally circular bristle holder 13 having a plurality of bristle tufts embedded therein, wherein each tuft 8 comprises a plurality of bristles. The handle provides compartments for holding an electric motor 14 and two batteries 15 and 16, although a rechargeable power source can be substituted for the batteries 15 and 16. A shaft coupling 17 is arranged to grip one end of the shaft 12 and allow the shaft to be pulled out for cleaning or replacement as will be described below.

Figure 2:
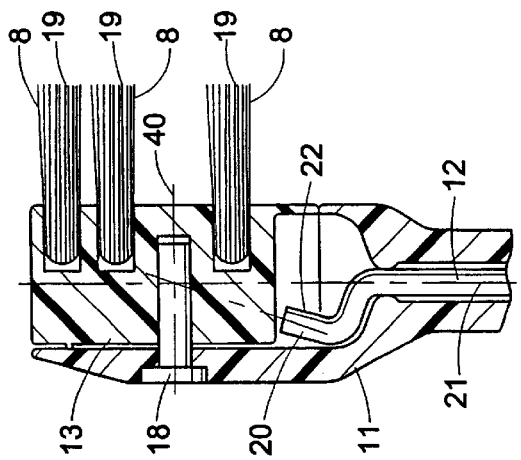
FIG. 2 shows a cross-sectional side view of part of the toothbrush of FIG. 1.

The head 11, as is better seen in FIG. 2, supports a post 18, which provides a rotational or oscillatory pivot axis 40 for the bristle holder 13. Bristles 19 are shown for illustrative purposes only in FIG. 2. The shaft 12 has an integrally formed remote-most end 20 that is offset from a central longitudinal axis 21 of the shaft. The remote-most end 20 fits into a slot 22 (see FIG. 3) formed in a side of the bristle holder 13. It will be noted that the end 20 points towards an intersection of the first axis 21 and the pivot axis 40 of the post 18. In one embodiment, the post is arranged so that the pivot axis 40 is substantially perpendicular to the central longitudinal axis 21 of the shaft. The pivot axis 40 is also substantially parallel to the direction in which the bristles 19 extend. While this arrangement is preferred, it is contemplated that the post 18 can be arranged differently. For example, the post 18 might be angled so that the pivot axis 40 is not substantially perpendicular to the longitudinal axis 21 of the shaft but rather forms an acute angle therewith in order to provide a wobbling or swiveling action about the pivot axis 40. When the shaft 12 is rotated by the motor 14, the remote end 20 describes a circle about the shaft 12 and drivingly engages the slot 22 to cause the bristle holder 13 to vibrate or oscillate about the pivot axis of the bristle holder 13. In this regard, the formed remote-most end 20 may be considered to be a cam or a gear tooth. To vibrate is to move to and fro or from side to side. To oscillate is to move or travel back and forth between two points. A cam is a shaped component or portion of a component, which determines the motion of a follower. As may be seen in FIG. 3, slot 22 is closed-ended and extends radially inward from the outer circumference of the holder to less than the distance to the center of the holder and between adjacent pairs of bristle holes. Thus, the bristle holder 13 pivots, oscillates, or rotates forwards and backwards about the center of the post 18. To pivot is to turn on or as if on a pivot. To rotate is to turn about an axis or a center. Such movement provides a first relative motion between the head 11 and the bristles 19 and is generally beneficial for efficient cleaning of teeth. The width of the slot 22 is preferably generally the same as the diameter of the end 20 to leave minimum play; this keeps noise to a minimum in use.

Figure 5:
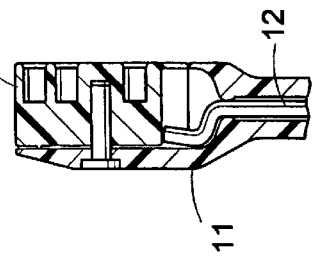

Preferably, the motor 14 runs at around 6000 rpm. Where desired, the motor can run at other speeds or be arranged to run at two or more speeds, selectable by the user. FIG. 1 shows a toothbrush where the holder 13 vibrates, oscillates, or rotates through an angle of 30 degrees. In FIG. 2, the angle is 35 degrees and in FIG. 5 the angle is 15 degrees. It will therefore be appreciated that the rotational angle can be chosen by fitting different shafts 12 and that the same bristle holder can be used for all angles.

Figure 3:
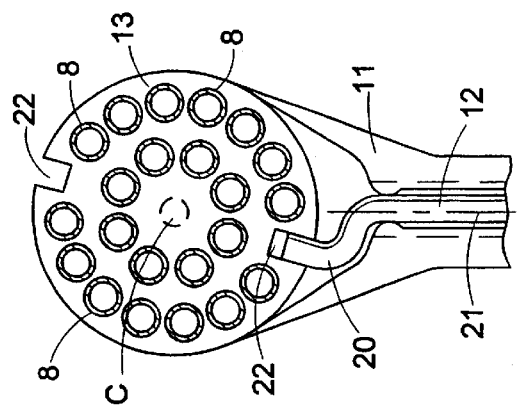
FIG. 3 is a sectional bottom view of FIG. 2.
Figure 6:
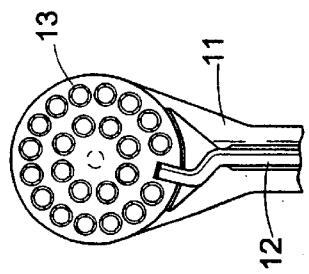

Each bristle holder 13 may be provided with more than one slot 22 as may be seen in FIG. 3, opposite each other so as to be better balanced or so that different slots can be used if the one slot wears or if the bristles wear unevenly in use. In other words, the holder 13 can then be set up in two or more rotational positions. The holder 13 is preferable easily removable from the head 11, by being spring clipped to the post 18 for example. Such removal allows better cleaning and storing in a hygienic container perhaps and also enables the shaft 12 to be readily withdrawn and replaced when required.

The described shafts 12 are preferably integrally formed, i.e., a single length of a thin rod and shaped as shown. However, it is possible to arrange for the remote end or cam 20 to be separately formed or provided and fixed to a straight end part of the shaft or elsewhere on the shaft. Such a separate part can be a brush having a central axis coinciding with the axis 21 of the shaft and an off-center driving post. The driving post then takes up the position and function of the remote end or cam 20. Thus, the driving post and the slot 22 then form the driving engagement between the shaft and the holder 13 and so the driving post can be regarded as the remote end of the shaft.

It is also possible, but not usually so convenient, in some embodiments of the invention to arrange for the holder 13 to be hingedly pivoted at one side, for example opposite the shaft. In such a case, bristles mounted nearer the hinged pivot will not actually move as much as bristles at the side next to the shaft but they will still vibrate significantly.

It will also be appreciated that whether pivoted to rotate or to hinge, the bristle holder 13 need not be circular. However, a circular holder 13 is normally preferred so that its rotational position can be changed when desired, as mentioned above.

While the above-described shaft arrangement is preferred, it is contemplated that other shaft arrangements can be used with the present invention. For example, the arrangement described in U.S. Pat. No. 5,732,432, the substance of which is incorporated herein by reference, might be substituted to accommodate mechanical misalignments of the shaft and mechanical strain during use. Further, the head 11 might be provided in a form in which it can be readily detached from the handle 10. This could be accomplished using, coupling arrangements for the shaft and body portion of the head. Such arrangements are known in the art. For example, the head and handle portions can include mating slots, spring clips, and protrusions and/or locking or securing tabs and grooves. The shaft can be divided into two sections, each section including a coupling element. For example the coupling is achieved with a keyed arrangement. For instance, coupling elements can include male and female mating splines affixed to respective shaft section ends, or as shown in U.S. Pat. No. 5,617,601, the substance of which is incorporated herein by reference. Further, the slot 22 might be replaced by a wobble plate, such as described in U.S. Pat. No. 5,784,743, the substance of which is incorporated herein by reference.

Figure 8:
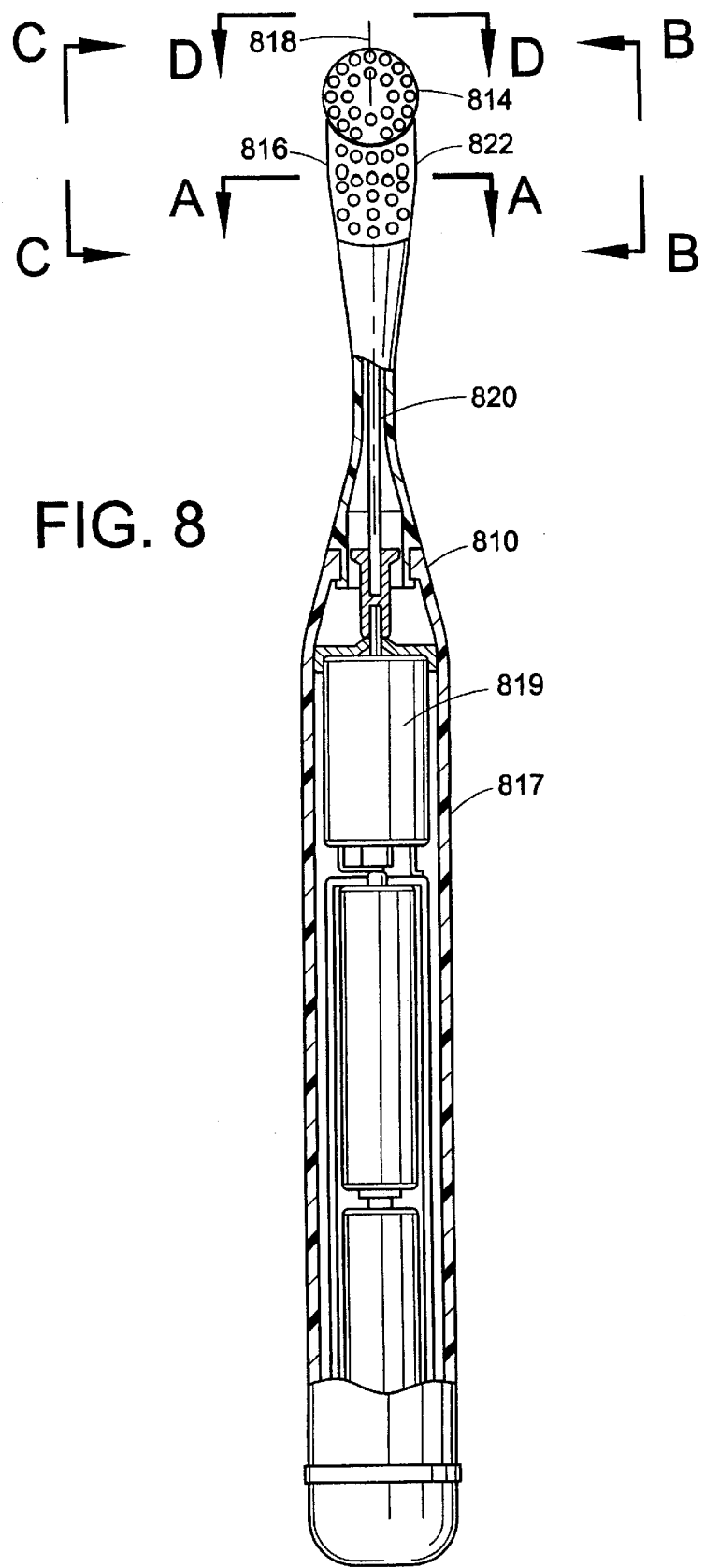
FIG. 8 is a bottom view of an enhanced toothbrush having a second bristle holder. The toothbrush is shown in partial section.
Figure 8A:
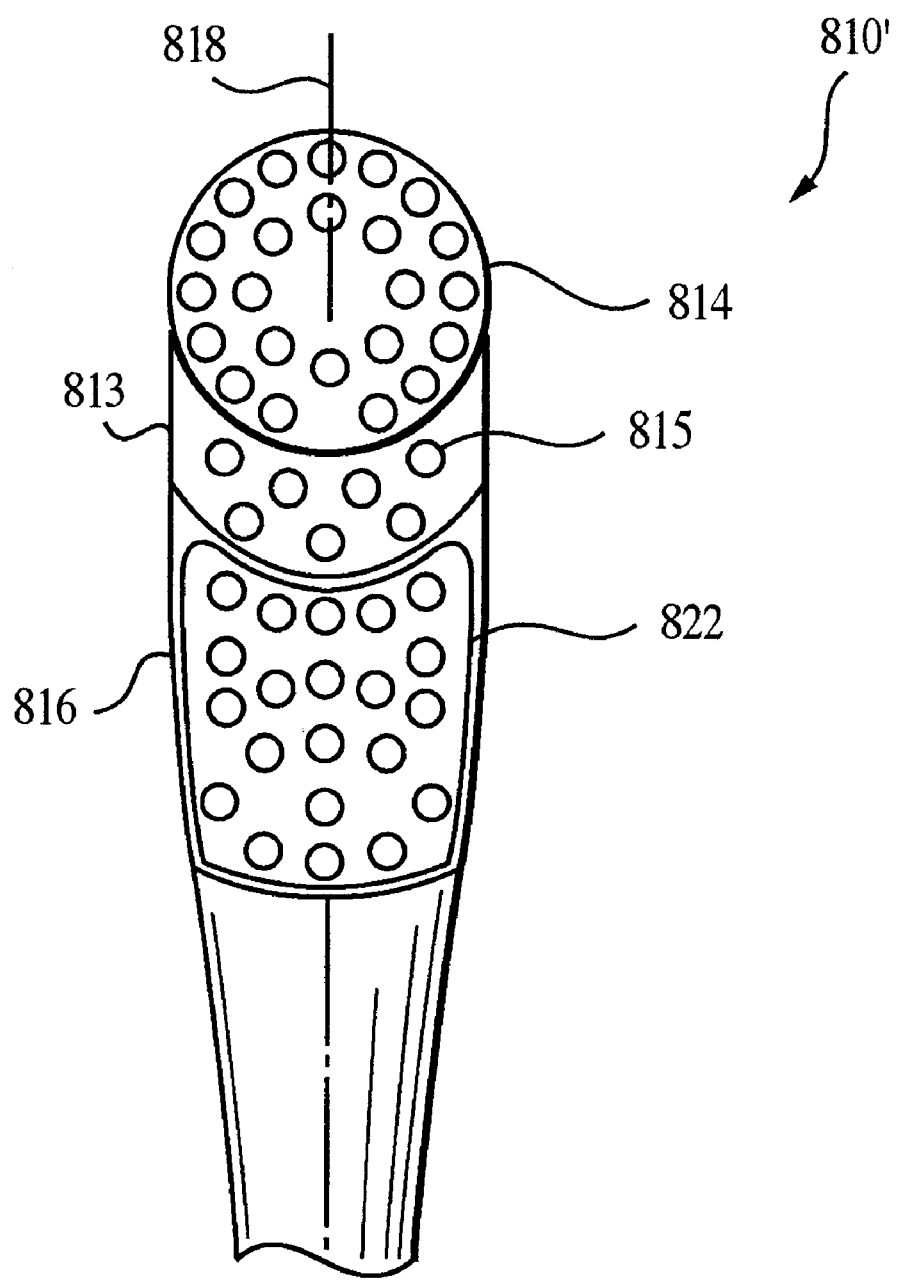
FIG. 8A is a detailed view of a head portion of an enhanced toothbrush having a first, a second, and a third bristle holder and a collection of static bristles.

With additional reference now to FIG. 8–FIG. 18, embodiments of an enhanced electric toothbrush 810 include a first bristle holder 814 similar to the bristle holder 13 described above. The enhanced toothbrush 810 has a head 816 and a body or handle 817. Of course, the enhanced toothbrush includes a motor 819 and batteries for powering the motor. The head portion 816 has a longitudinal axis 818. The first bristle holder 814 is illustrated as circular. However, other shape bristle holders are contemplated and within the scope of the invention. The first bristle holder 814 includes at least one slot as described above (see FIG. 3) for receiving a remote-most end or cam of a driving shaft 820 as described in reference to FIG. 1–FIG. 7. The remote-most end (see FIG. 3) of the driving shaft is bent or offset from a central longitudinal axis 21 (see FIG. 3) of the driving shaft 820 as described above. The motor 819 is operative to rotate the shaft 820. In short, with regard to the construction and operation of the shaft 820 in relation to the first bristle holder 814, the enhanced toothbrush 810 is similar to the toothbrush described in reference to FIG. 1–FIG. 7. However, embodiments of the enhanced electric toothbrush 810 also include second bristle holders disposed adjacent the first bristle holders, such as second bristle holder 822. While it is desirable to locate the second bristle holder directly adjacent the first bristle holder, it is contemplated that a gap may be provided between the first and second bristle holders. In addition, the space between the movable first and second bristle holders might be filled with stationery or fixed bristles which are embedded in a fixed or stationary third bristle holder (not shown) which forms part of the toothbrush head. FIG. 8A illustrates a variant embodiment of the toothbrush 810 shown in FIG 8. The toothbrush 810' of FIG. 8A further includes a plurality of stationary bristles 815 disposed between the first and second bristle holders and retained within a third bristle holder 813. In many embodiments of the enhanced electric toothbrush, the second bristle holders are movable and separately associated with, and separately driven by, a driving shaft such as the driving shaft 820. The movable second bristle holders are movable in directions and/or manners that are different and distinct from whichever of the rotary or hingedly pivoted vibratory movements, described in reference to FIG. 1–FIG. 7, is used in the particular embodiment.

Figure 9:
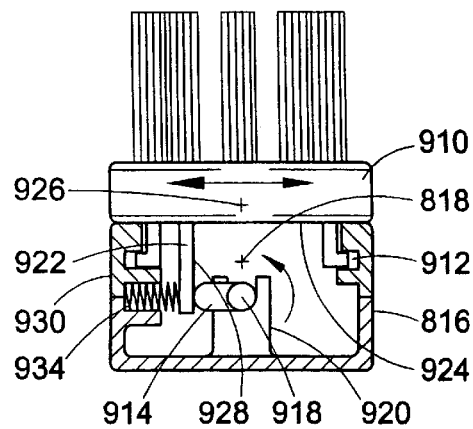
FIG. 9 is a sectional view taken along A—A in FIG. 8 of a first embodiment of a toothbrush head portion.
Figure 9A:
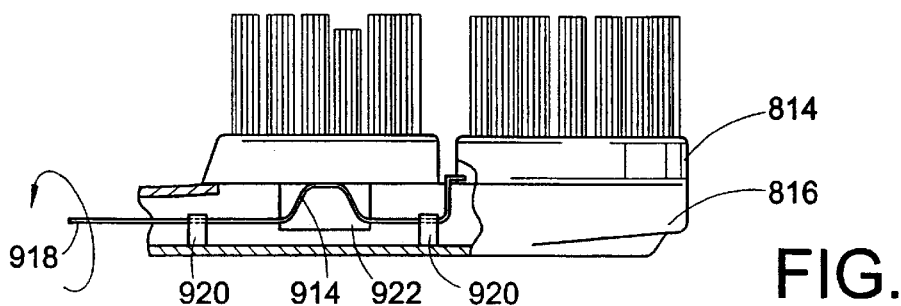
FIG. 9A is a partial sectional side view of the first embodiment.
Figure 12:
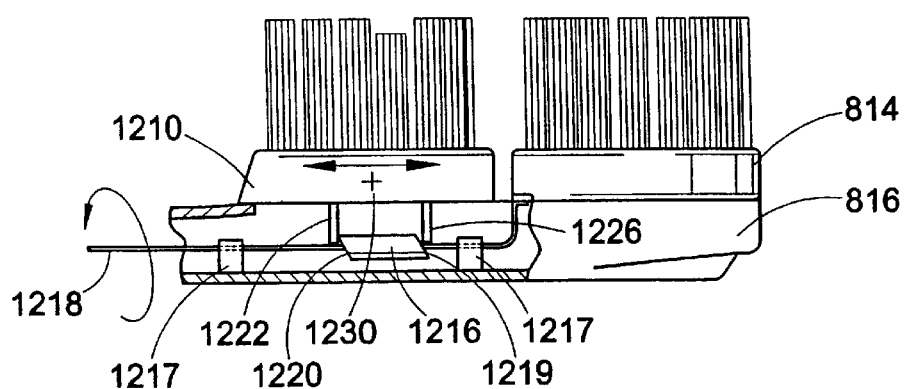
FIG. 12 is a partial sectional view taken along B—B in FIG. 8 of a fourth embodiment of a toothbrush head.
Figure 13:
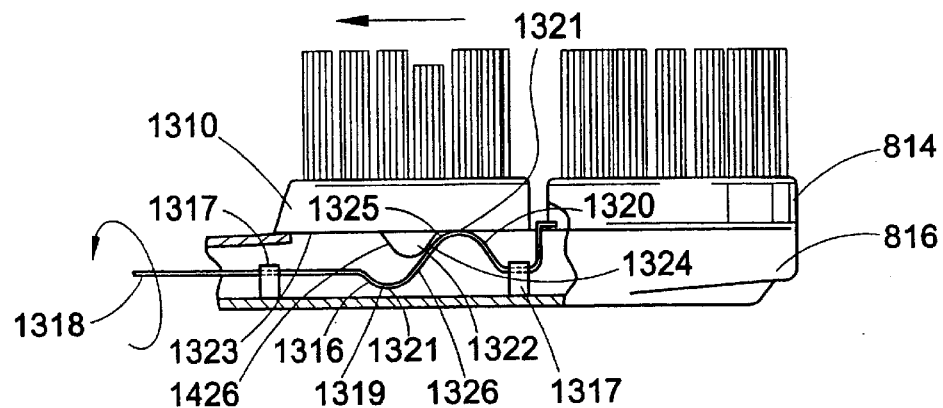
FIG. 13 is a partial sectional view taken along B—B in FIG. 8 of a fifth embodiment a toothbrush head.
Figure 15:
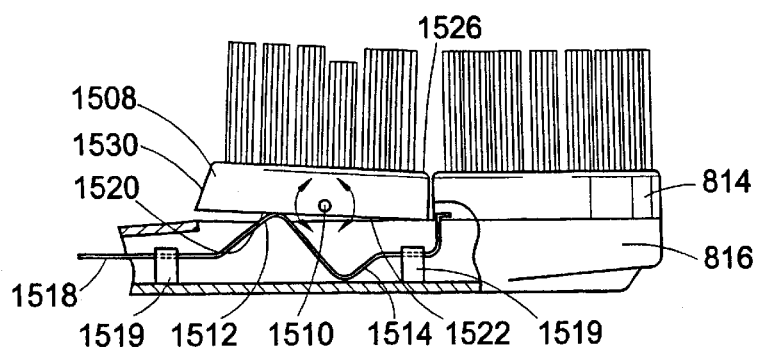
FIG. 15 is a partial sectional view taken along B—B in FIG. 8 of a sixth embodiment of a toothbrush head.

For example, referring to FIG. 9, a second bristle holder 910 is movably mounted in slots 912 in the toothbrush head 816 and separately driven in a vibratory, side-to-side, motion in a direction substantially perpendicular to the direction of the longitudinal axis 818 by an eccentric cam 914 included on a driving shaft 918. The cam 914 and other cams described below can comprise one or more bends in the shaft 918, as shown for example, example in FIG. 9A and as seen in views of other embodiments described below such as seen in FIG. 12, FIG. 13, and FIG. 15. Alternatively, the cam 914 can be provided as a separate piece, which is attached to the shaft 918 by adhesive, a press or snap fit, a co-molding or any other mechanical or chemical means known in the art. Optionally, the driving shaft is supported by a shaft support 920. A cam follower 922 depends from a bottom surface 924 of the second bristle holder 910. The cam follower 922 is offset from a longitudinal axis 926 of the second bristle holder. As the motor 819 of the enhanced toothbrush 810 rotates the shaft 918, the cam 914 comes into contact with a cam contact surface 928 of the cam follower 922 and drives the cam follower 922, and therefore, the second bristle 910 holder toward one side 930 of the enhanced toothbrush 810 and away from the longitudinal axis 818 of the head portion 816. As the shaft 918 continues to rotate, the cam 914 becomes disengaged with the cam follower 922. A resilient biasing member such as a spring 934, lodged between a wall of the head portion 816 and a second surface of the cam follower, urges the cam follower 922, and therefore the second bristle holder 910, back toward the longitudinal axis 818 of the head portion 816. As this back and forth or sided to side motion is repeated (as the shaft 918 continues to rotate), a sweeping or brushing motion is provided that is distinct from and complimentary to the motion provided by the first bristle holder 814. The stroke and/or frequency of the second bristle holder 910 can be changed by varying the construction of the spring and placement and/or sizing of the cam 914 and the cam follower 922. For example, the cam follower 922 might be placed closer to the axis 926 to provide a shorter stroke for the cam follower 922, or a stronger spring might be provided to increase the rate of return of the second bristle holder 910 or more than one spring might be provided. Alternatively, the cam follower 922 might form an acute angle with the bottom surface 924 of the second bristle holder 910 or the first surface can be provided as accurate, curvilinear, or in other complex forms as opposed to the planar surface shown in FIG. 9.

Figure 10:
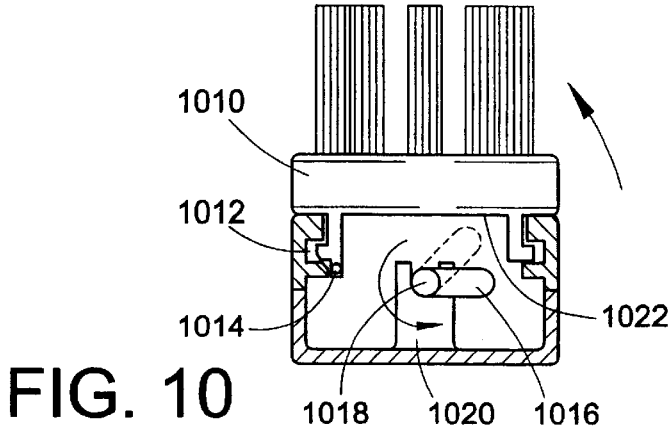
FIG. 10 is a sectional view taken along A—A in FIG. 8 of a second embodiment of a toothbrush head portion.

Referring to FIG. 10, in a second embodiment of the enhanced toothbrush 810 a second bristle holder 1010 is movably mounted in slots 1012 in the toothbrush head 816 and separately driven in a vibratory, swinging or pivoting motion about a hinge or pivot 1014, by a cam 1016 included on a driving shaft 1018. The cam 1016 can comprise one or more bends in the shaft 1018 or be provided as a separate piece as previously discussed. Optionally, the driving shaft is supported by a shaft support 1020. A cam contact surface 1022 is located on a bottom surface of the second bristle holder 1010. As the motor 819 of the enhanced toothbrush 810 rotates the shaft 1018, the cam 1016 comes into contact with the cam contact surface 1022 and drives or pushes the second bristle holder 1010 causing the second bristle holder to swing or pivot about the hinge or pivot 1014. As the shaft 1018 continues to rotate, the cam 1016 becomes disengaged with the cam contact surface 1022. During use, as the cam 1016 comes in contact with the cam contact surface 1022, bristles of the second bristle holder 1010 are urged against the users teeth with greater force. Preferably, bristles of the second bristle holder 1010 are urged between the teeth of the user to provide a cleaning and flossing function. As the cam disengages with the contact surface 1022, bristles pressing against the teeth of the user urge the second bristle holder away from the users teeth. As this swinging or pivoting motion is repeated (as the shaft 1018 continues to rotate), a flossing or deep cleaning motion is provided that is distinct from and complimentary to the motion provided by the first bristle holder 814.

Figure 11:
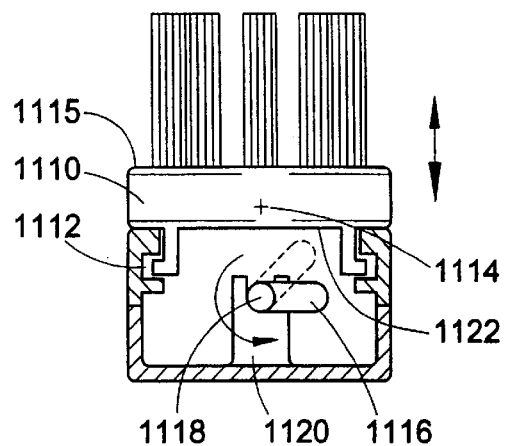
FIG. 11 is a sectional view taken along A—A in FIG. 8 of a third embodiment of a toothbrush head portion.

Referring to FIG. 11, in a third embodiment of the enhanced toothbrush 810 a second bristle holder 1110 is movably mounted in slots 1112 in the toothbrush head 816 and separately driven in a vibratory, lifting or vertical pulsating motion (e.g., in a direction substantially perpendicular to the longitudinal axis 1114 and substantially parallel to a surface 1115 of the second bristle holder 1110 as shown by way of example in FIG. 11) within the slots 1112, by a cam 1116 included on a driving shaft 1118. Optionally, the driving shaft is supported by a shaft support 1120. The cam 1116 can comprise one or more bends in the shaft 1118 or can be provided as a separate piece as previously discussed. A cam contact surface 1122 is located on a bottom surface of the second bristle holder 1110. As the motor 819 (see FIG. 8) of the enhanced toothbrush 810 rotates the shaft 1118, the cam 1116 comes into contact with the cam contact surface 1122 and drives or lifts, in a vibratory, lifting, or vertical pulsating motion, the second bristle holder 1110 causing the second bristle holder to lift or pulsate in a direction away from the head portion 816 and toward the teeth of a toothbrush user (not shown). As the shaft 1118 continues to rotate, the cam 1116 becomes disengaged with the cam contact surface 1122. During use, as the cam 1016 comes in contact with the cam contact surface 1122, bristles of the second bristle holder 1110 are urged against the users teeth with varying degrees of force. Preferably, bristles of the second bristle holder 1110 are urged between the teeth of the user to provide a cleaning and flossing function. As the cam disengages with the contact surface 1122, bristles pressing against the teeth of the user urge the second bristle holder away from the users teeth and back toward the head portion 816. As this lifting or vertical pulsating motion is repeated (as the shaft 1018 continues to rotate), a flossing or deep cleaning motion is provided that is distinct from and complimentary to the motion provided by the first bristle holder 814.

Referring to FIG. 12, in a fourth embodiment of the enhanced toothbrush 810 a second bristle holder 1210 is movably mounted in slots (not shown, but similar to the slots 912 illustrated in FIG. 9) in the toothbrush head 816 and separately driven in a reciprocating or translating, longitudinal motion within the slots by a cam 1216 included on a driving shaft 1218. Optionally, the shaft is supported by shaft supports 1217. The shaft supports may include C or U shaped portions (not shown) that are operative to receive and snap around the shaft. Other means for retaining a shaft in a support are known in the art. The cam 1216 can comprise a shaped bead, with an appropriate eccentric configuration, placed or molded over and firmly secured to the shaft 1218. In one embodiment, the cam 1216 includes a pair of acutely angled surfaces 1219, 1220 which are inclined in the same direction and at the same angle of inclination, but which are disposed at opposite ends of the cam 1216. The direction of inclination and angle of inclination can be varied as desired to change the frequency and stroke of the second bristle holder 1210. First 1222 and second 1226 cam followers depend from a bottom surface of the second bristle holder 1210. The cam followers 1222, 1226 are offset or spaced from a transverse axis 1230 of the second bristle holder. The cam followers 1222, 1226 straddle and/or capture the cam 1216 so that the angled surfaces 1219, 1220 slidably engage the free ends of the cam followers 1222 and 1226. As the motor 819 (see FIG. 8) of the enhanced toothbrush 810 rotates the shaft 1218, the first acutely angled surface 1220 of the cam 1216 comes into contact with a surface of the first cam follower 1222 and drives the cam follower, and therefore, the second bristle holder 1210, away from the first bristle holder 814 along the longitudinal axis 818 of the head portion 816. As the shaft 918 continues to rotate, the cam 1216 becomes disengaged with the first cam follower 1222. The second acutely angled second surface 1219 of the cam 1216 then comes into contact with a surface of the second cam follower 1226 and drives the second cam follower 1226, and therefore, the second bristle holder 1210, back toward the first bristle holder 814. As this back and forth motion is repeated (as the shaft 918 continues to rotate), a scrubbing action is provided by the reciprocating or translating motion that is distinct from and complimentary to the motion provided by the first bristle holder 814.

Figure 14:
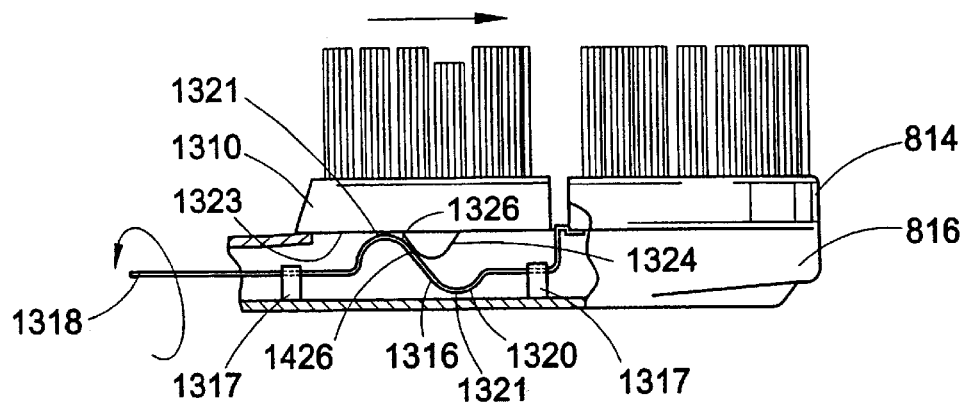
FIG. 14 is a partial sectional view taken along B—B in FIG. 8 of the fifth embodiment of a toothbrush head. A shaft is shown rotated to a different position than shown in FIG. 13.

Referring to FIG. 13 and FIG. 14, in a fifth embodiment of the enhanced toothbrush 810 a second bristle holder 1310 is movably mounted in slots (not shown, but similar to the slots 912 illustrated in FIG. 9) in the toothbrush head 816 and separately driven in an reciprocating or translating, longitudinal motion, by a cam 1316 included on a driving shaft 1318. Optionally, the shaft is supported by shaft supports 1317. The shaft supports may include C or U shaped portions (not shown) that are operative to receive and snap around the shaft. Other means for retaining a shaft in a support are known in the art. The cam 1316 is sinusoidal or curvilinear in nature in that it has one or more adjacent arcuate bends 1319 and 1320 in the shaft 1318. The arcuate bends 1319, 1320 have each have an apex 1321, and the apexes 1321 are disposed on opposite sides of the driving shaft 1318. A cam follower 1322 depends from a bottom surface 1323 of the second bristle holder 1310 and is disposed between the apexes 1321 of the cam 1316. As the motor 819 of the enhanced toothbrush 810 rotates the shaft 1318, a first surface 1325 of the cam 1316 comes into contact with a first surface 1324 of the cam follower 1322 and drives the cam follower 1322, and therefore, the second bristle holder 1310 away from the first bristle holder 814 in a direction along the longitudinal axis 818 of the head portion 816. As the shaft 918 continues to rotate, the apex 1321 passes and becomes disengaged with the first cam follower surface 1324. A second surface 1326 of the cam 1316 then comes into contact with a second surface 1426 of the cam follower 1322 and drives the cam follower 1322, and therefore, the second bristle holder 1310 back toward the first bristle holder 814. As this back and forth motion is repeated (as the shaft 918 continues to rotate), a scrubbing action is provided by the reciprocating or translating motion that is distinct from and complimentary to the motion provided by the first bristle holder 814. The stroke and frequency of the reciprocating or translating motion can be varied by changing the spacing between the apexes and/or the amplitude, shape, or height of the apexes.

Referring to FIG. 15, in a sixth embodiment of the enhanced toothbrush 810, a second bristle holder 1508 is movably mounted to the toothbrush head 816 with a pivot 1510, which can be provided in the form of a pin or hinge. The pivot 1510 is installed at a centrally located transverse axis of the second bristle holder 1508. In one embodiment, the second bristle holder 1508 pivots about a pin, which is anchored in the sidewalls of the toothbrush neck or head 816 at the midpoint of the second bristle holder 1508. The second bristle holder 1508 is separately driven in a vibratory, swinging, teetering or rocking motion by a cam comprised of first 1512 and second 1514 cam portions included on a driving shaft 1518. Optionally, the shaft is supported by shaft supports 1519. The shaft supports may include C or U shaped portions (not shown) that are operative to receive and snap around the shaft. Other means for retaining a shaft in a support are known in the art. The cam portions 1512, 1514 can comprise one or more rectilinear, curvilinear or other bends in the shaft 1518. As is illustrated in FIG. 15 the first cam portion 1512 is located adjacent a first side of the pivot and the second cam portion 1514 is located adjacent a second side of the pivot. The second cam portion 1514 can comprise a portion of the remote-most end or cam (not shown but similar to the remote-most end or cam 20 of FIG. 3) of the shaft 1518. First 1520 and second 1522 cam contact surfaces are located on a bottom surface of the second bristle holder 1508. As is the case with all the described embodiments, the amplitude or height of the bends or eccentricities that make up the first and second cam portions 1512, 1514 are large enough reach the related cam contact surface(s) and to drive the second bristle holder a desired distance toward, into, across or along a toothbrush users teeth. Changing the distance between the apexes and the pivot point can vary the required amplitude or height. Changing the distance between the apexes and the pivot point may affect a required or desired torque delivered by the motor 819. As the motor 819 of the enhanced toothbrush 810 rotates the shaft 1518, the first cam portion 1512 comes into contact with the first cam contact surface 1520 and drives or lifts (relative to the figure) a first end 1522 of the second bristle holder 1510 causing the first end 1522 to rock or move about the pivot 1510 in a direction away from the head portion 816 and toward the teeth of a toothbrush user (not shown). This action lowers a second end 1526 of the second bristle holder back toward the head portion 816. As the shaft 1518 continues to rotate, the first cam portion 1512 becomes disengaged with the first cam contact surface 1520 and the second cam portion 1514 engages the second cam contact surface 1522. The second cam portion 1514 drives or lifts (relative to the figure) the second end 1526 of the second bristle holder 1508 causing the second end 1522 to rock or move about the pivot 1510 in a direction away from the head portion 816 and toward the teeth of the toothbrush user. This action lowers a first end 1530 of the second bristle holder back toward the head portion 816. During use, as the first and second cam portions 1512, 1514 alternately come in contact with the first and second cam contact surfaces 1520, 1522, bristles of the second bristle holder 1508 are urged against teeth of the user with varying degrees of force. Preferably, bristles of the second bristle holder 1508 are urged between the teeth of the user to provide a cleaning and flossing function. As the rocking or pivoting motion is repeated (as the shaft 1518 continues to rotate), a flossing or deep cleaning motion is provided that is distinct from and complimentary to the motion provided by the first bristle holder 814.

Figure 16:
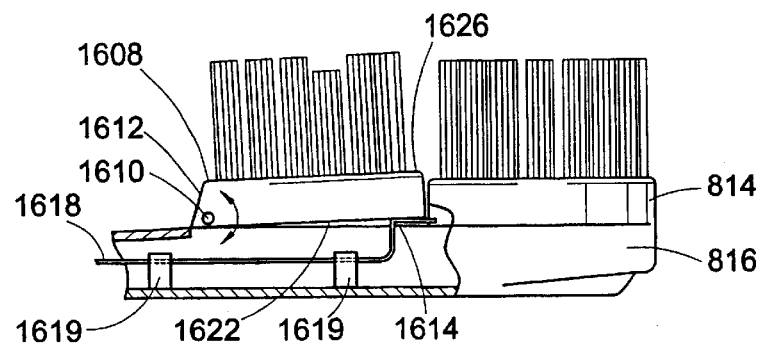
FIG. 16 is a partial sectional view taken along B—B in FIG. 8 of a seventh embodiment of a toothbrush head.

Referring to FIG. 16, in a seventh embodiment of the enhanced toothbrush 810 a second bristle holder 1608 is movably mounted to the toothbrush head 816 with a pivot 1610, which can be provided in the form of a pin or of a hinge installed at a transverse axis of the second bristle holder 1608. In one embodiment, the second bristle holder 1608 pivots about a pin, which is anchored in the sidewalls of the toothbrush neck at the midpoint of the second bristle holder 1608. The transverse axis is, for example, adjacent to a first end 1612 of the second bristle holder 1608. The second bristle holder 1608 is separately driven in a vibratory, swinging, pivoting or rocking motion by a cam 1614 included on a driving shaft 1618. Optionally, the shaft is supported by shaft supports 1619. The shaft supports may include C or U shaped portions (not shown) that are operative to receive and snap around the shaft. Other means for retaining a shaft in a support are known in the art. The cam 1614 may be a portion of a remote-most end of the shaft 1618 (not shown but similar to the remote-most end or cam 20 of FIG. 3). The cam 1614 can comprise one or more bends in the shaft 1618. For example, the bends can be rectilinear, curvilinear or other kinds of bends. A cam contact surface 1622 is located on a bottom surface of the second bristle holder 1608 adjacent to a second end 1626 thereof. As the motor 819 of the enhanced toothbrush 810 rotates the shaft 1618, the cam 1614 comes into contact with the cam contact surface 1622 and drives or lifts (relative to the figure) the second end 1626 of the second bristle holder 1608 causing the second end 1626 of the second bristle holder 1608 to rock or move about the pivot 1610 in a direction away from the head portion 816 and toward the teeth of a toothbrush user (not shown). As the shaft 1618 continues to rotate, the cam 1614 becomes disengaged with the cam contact surface 1622. During use, as the cam 1614 comes in contact with the cam contact surface 1622, bristles of the second bristle holder 1608 are urged against teeth of the user with a varying degree of force. Preferably, bristles of the second bristle holder 1608 are urged between the teeth of the user to provide a cleaning and flossing function. As the cam disengages with the contact surface 1622, bristles pressing against the teeth of the user urge the second bristle holder away from the users teeth and back toward the head portion 816. As this swinging or pivoting motion is repeated (as the shaft 1618 continues to rotate), a flossing or deep cleaning motion is provided that is distinct from, and complimentary to, the motion provided by the first bristle holder 814.

Figure 17:
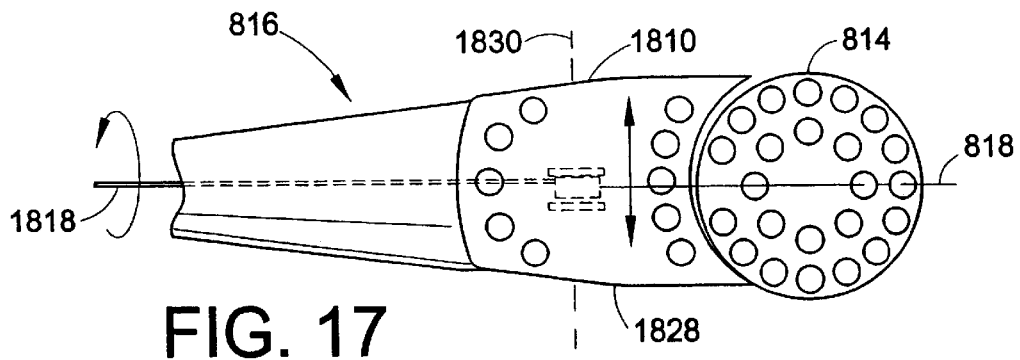
FIG. 17 is a bottom view of a head portion of a ninth embodiment of a toothbrush.
Figure 18:
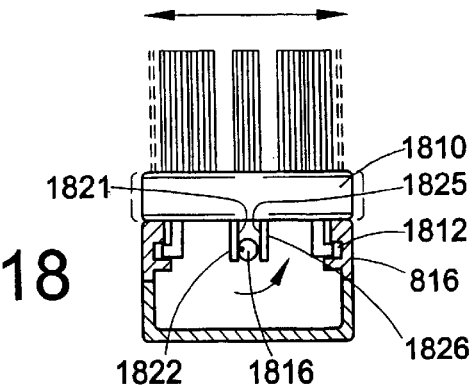
FIG. 18 is a partial sectional view taken along B—B in FIG. 8 of the ninth embodiment of a toothbrush head.

Referring to FIG. 17 and FIG. 18, in a eighth embodiment of the enhanced toothbrush 810 a second bristle holder 1810 is movably mounted in slots 1812 in the toothbrush head 816 and separately driven in a reciprocating or translating, transverse motion within the slots 1812 by a cam 1816 included on a driving shaft 1818. The cam 1816 can comprise an appropriately shaped bead placed over or molded and fixedly secured to the shaft 1818. For example, the bead is shaped as and eccentric cam. Alternatively, the cam can include one or more rectilinear, curvilinear or other kind of bend. First 1822 and second 1826 cam followers depend from a bottom surface of the second bristle holder 1810. The cam followers are, for example, offset from the longitudinal axis 818 of the second bristle holder and straddle or capture the cam 1816. As the motor 819 (see FIG. 8) rotates the shaft 1818, the cam 1816 comes into contact with a surface 1821 of the first cam follower 1822 and drives the first cam follower 1822, and therefore, the second bristle holder 1810 away from a first side 1828 of the head portion 816 along a transverse axis 1830 of the head portion 816. As the shaft 1818 continues to rotate, the cam 1816 becomes disengaged with the first cam follower 1822. The cam 1816 then comes into contact with a surface 1825 of the second cam follower 1826 and drives the second cam follower 1826, and therefore, the second bristle holder 1810 back toward the first side 1828 of the head portion 816. As this back and forth or side to side motion is repeated (as the shaft 918 continues to rotate), a sweeping motion is provided that is distinct from and complimentary to the motion provided by the first bristle holder 814.

Figure 19:
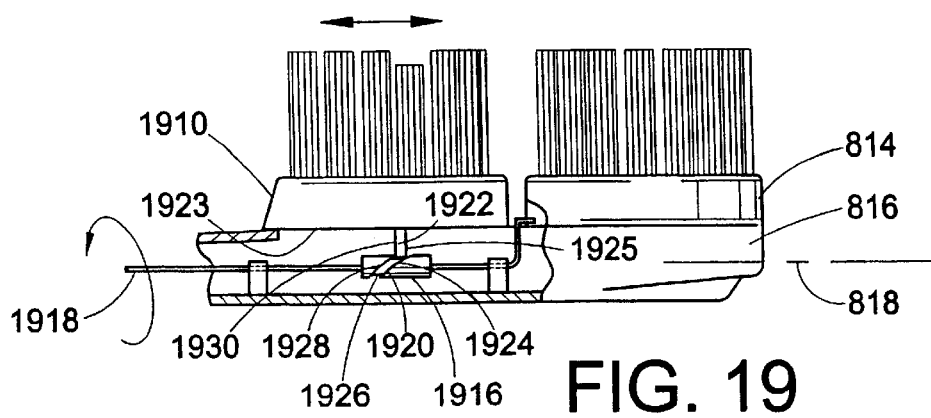
FIG. 19 is a partial sectional view taken along B—B in FIG. 8 of a tenth embodiment of a toothbrush head.

Referring to FIG. 19 in a ninth embodiment of the enhanced toothbrush 810 a second bristle holder 1910 is movably mounted in slots (not shown) in the toothbrush head 816 and separately driven in an reciprocating or translating, longitudinal motion, by a cam 1916 included on a driving shaft 1918. The cam 1916 can comprise a shaped bead, with an appropriate configuration, placed or molded over and firmly secured to the shaft 1918. The cam 1916 includes a reversing spiral or helical groove 1920. The spiral or helical groove extends around a circumference of the bead and spirals about a longitudinal axis of the bead. For example, the longitudinal axis coincides with the shaft 1918. A cam follower 1922 depends from a bottom surface 1923 of the second bristle holder 1910. The cam follower 1922 is slidingly received within the spiral groove 1920. As the motor 819 of the enhanced toothbrush 810 rotates the shaft 1918, a first surface 1924 of the spiral groove 1920 comes into contact with a first surface 1925 of the cam follower 1922 and drives the cam follower 1922, and therefore, the second bristle holder 1910 away from the first bristle holder 814 along the longitudinal axis 818 of the head portion 816. As the shaft 1918 continues to rotate, the cam follower 1922 reaches an apex 1926 of the spiral groove 1920 and the first surface 1924 of the spiral groove 1920 becomes disengaged with the first cam surface 1925. A second surface 1928 of the spiral groove 1920 then comes into contact with a second surface 1930 of the cam follower 1922 and drives the cam follower 1922, and therefore, the second bristle holder 1910 back toward the first bristle holder 814. As this back and forth motion is repeated (as the shaft 1918 continues to rotate), a scrubbing motion is provided that is distinct from and complimentary to the motion provided by the first bristle holder 814. Optionally cam 1916 is eccentrically mounted on the shaft 1918 and the longitudinal axis of the bead or cam 1916 does not coincide with the shaft 1918. In this case, if the cam follower 1922 is made long enough to ride on the bottom of the spiral groove 1920, a lifting or vertical pulsing force is provided to the second bristle holder as the eccentrically mounted came is rotated by the shaft. Alternately, or additionally, the depth of the groove is varied. The variation in depth provides lifting or vertical pulsing forces to the cam follower and therefore to the second bristle holder. In either case, the second bristle holder is made to pulsate vertically in addition to the reciprocating or translating motion. The spiral groove may be replaced with a groove that cycles back and forth along the longitudinal axis of the bead several times as it circles the bead. This sort of groove can be used to increase the reciprocating frequency of the second bristle holder.

Figure 20:
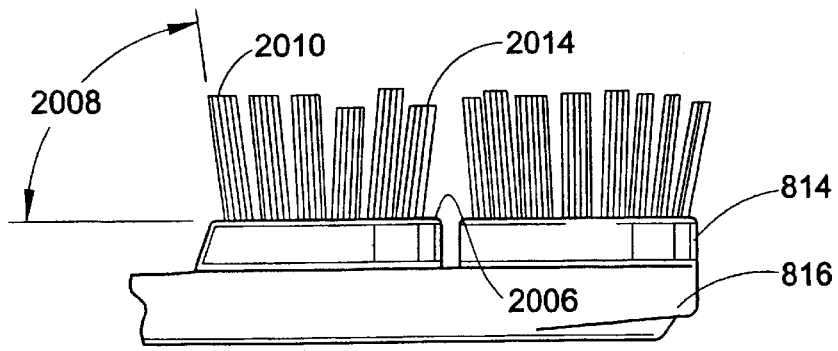
FIG. 20 is a side view of a toothbrush showing a first exemplary alternate bristle arrangement.
Figure 21:
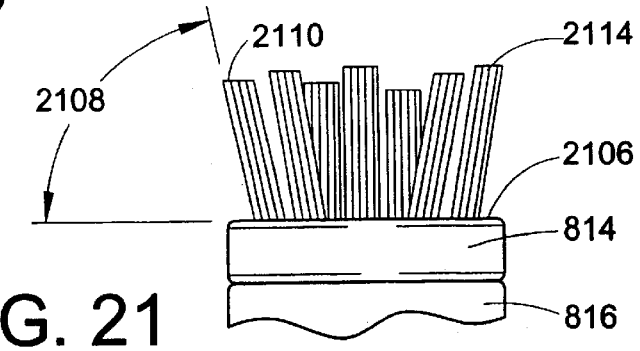
FIG. 21 is an end view taken along D—D of FIG. 8 showing a second exemplary bristle arrangement.

While the embodiments of the present invention have been illustrated for simplicity with bristles, which extend in a direction substantially perpendicular to the longitudinal axis 818 and the surface (for example see 1115 of FIG. 11) of the bristle holders, it is contemplated that the bristles might be arranged differently to complement or further enhance the motions of the first and/or second bristle holders. Referring to FIG. 20, some or all of the bristles might extend in a direction which forms an acute angle 2008 to a surface 2006 of the bristle holder and extends in a direction toward or away from the handle, such as shown by way of example in FIG. 20 with respect to bristles 2010 and 2014 respectively. Referring to FIG. 21, in another embodiment, some of the bristles might extend outwardly away from head, in another direction, again forming an acute angle 2108 with respect to the surface of the bristle holder, as shown by way of example in FIG. 21 with respect to bristles 2110 and 2114. Massaging bristles or bristles of varying height might also be used, such as described in U.S. Pat. Nos. Des. 330,286, Des. 434,563, the substances of which are incorporated herein by reference. Other preferred bristle arrangements suitable for use include those arrangements described in whole or part in U.S. Pat. Nos. 6,006,394; 4,081,876; 5,046,213; 5,335,389; 5,392,483; 5,446,940; 4,894,880; and international publication no. WO 99/23910; the substances of which are incorporated herein by reference.

The described embodiments have been described with certain words and phrases that attempt to describe certain motions. Motion can either be constant or vibratory. One example of a constant motion is simple rotation where an element angularly moves in a single direction (e.g., a bristle holder which only rotates clockwise or swivels clockwise in a cone like envelope) or translates in a single direction. Vibration is any periodic movement having repeated cycles. Vibratory motion can have one or more frequencies and amplitudes. Vibratory movement which is substantially linear is referred to herein as a reciprocating motion. Reciprocating motion can occur in a number of directions, such as substantially horizontal, substantially vertical (i.e., a lifting or pulsating motion), and combinations thereof. Vibratory movement which is substantially rotational in nature is referred to herein as an oscillatory or pivoting motion.

Because most motions can be complex in nature (i.e., include elements of other types of motion), the use of the above-described terms herein can include other motions, unless stated otherwise (e.g., reciprocates only), in addition to the basic or primary motion described by the term. So, for example, a motion which is described herein as reciprocating may also include other vibratory or constant movements even though the primary movement is reciprocatory in nature.

Figure 22:
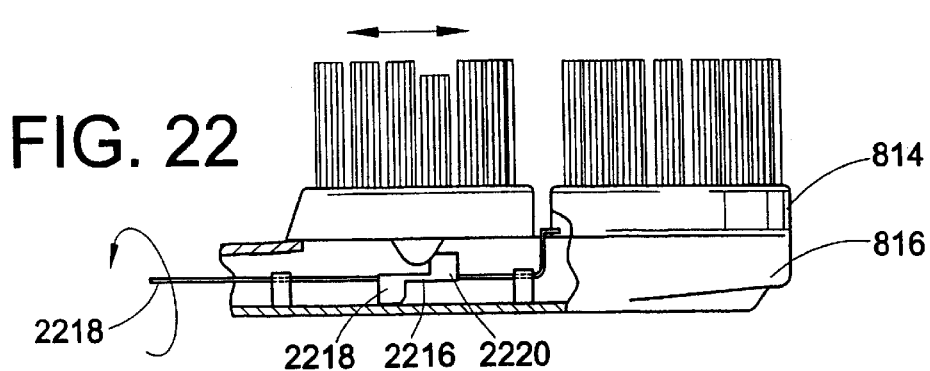
FIG. 22. is a partial sectional view taken along B—B in FIG. 8 of a second implementation of the fifth embodiment showing an alternate cam design.

The invention has been described with reference to particular embodiments. Modifications and alterations will occur to others upon reading and understanding this specification. For example, while certain have been described as comprising bends in a shaft and other cams have been described as including appropriately shaped beads secured to a shaft, the cams are not limited to the suggested form. Indeed, bends may be substituted for beads and beads may be substituted for bends. For example, FIG. 22 illustrates a tenth embodiment that is similar to the fifth embodiment illustrated in FIGS. 13 and 14. However, in the tenth embodiment the cam 2216 is formed as an appropriately configured complex bead fixedly placed or co-molded over the shaft 2218. The cam 2216 provides shapes 2218, 2220 with surfaces that serve an equivalent purpose to the arcuate bends 1319, 1320 described in reference to the fifth embodiment. Where first and second cam portions or surfaces are described or referenced, the portions or surfaces can be considered to be or implemented as separate cams. Where cams or cam portions are illustrated with one eccentricity or bent shape, multiple eccentricities or bent shapes may be included. Each added eccentricity or bent shape would increase the frequency with witch the related bristle holder vibrates, pulses, pivots, swivels, rocks, oscillates, reciprocates or translates. Additionally, where multiple eccentricities are included, they may be of varying amplitude, thereby providing varying bristle holder movement amplitudes. It is intended that all such modifications and alterations are included insofar as they come within the scope of the appended claims or equivalents thereof

What is claimed is:

1. An electric toothbrush, comprising:
   a handle at a first end of the toothbrush having a motor disposed therein;
   a head at a second end of the toothbrush, the head having a longitudinal axis, the head having a first bristle holder with a plurality of bristle tufts and a second bristle holder with a plurality of bristle tufts; and
   a rotatable shaft operatively connected to the motor and having a longitudinal axis and a cam, wherein the cam engages the second bristle holder to move the second bristle holder in a direction generally perpendicular to the longitudinal axis of the rotatable shaft, and wherein the rotatable shaft engages the first bristle holder to oscillate or rotate the first bristle holder about an axis generally perpendicular to the longitudinal axis of the rotatable shaft, and wherein the second bristle holder moves in a direction general parallel with the axis of the first bristle holder.

2. The electric toothbrush of claim 1, wherein a gap is defined between the first bristle holder and the second bristle holder.

3. The electric toothbrush of claim 2, wherein the head further comprises static bristles.

4. The electric toothbrush of claim 3, wherein the static bristles are disposed in the gap.

5. The electric toothbrush of claim 1, wherein the second bristle holder is disposed between the handle and the first bristle holder.

6. The electric toothbrush of claim 1, wherein the cam is a bend in the rotatable shaft.

7. The electric toothbrush of claim 6, wherein the second bristle holder has a cam contact surface for engaging the bend of the rotatable shaft.

8. The electric toothbrush of claim 7, wherein the cam contact surface is located on a bottom surface of the second bristle holder.

9. The electric toothbrush of claim 1, wherein the first bristle holder is driven by a remote-most end of the rotatable shaft.

10. The electric toothbrush of claim 9, wherein the remote-most end is displaced from the cam.

11. The electric toothbrush of claim 10, wherein the head further comprises a shaft support disposed between the first bristle holder and the second bristle holder.

12. The electric toothbrush of claim 9, wherein the remote-most end of the rotatable shaft is offset from the longitudinal axis of the rotatable shaft and engages a slot in the first bristle holder.

13. The electric toothbrush of claim 1, wherein the rotatable shaft passes under the second bristle holder and does not pass under the first bristle holder.

14. The electric toothbrush of claim 1, wherein the cam disengages from the second bristle holder such that during disengagement between the cam and the second bristle holder, the second bristle holder is movable towards the head of the toothbrush.

15. The electric toothbrush of claim 1, wherein the second bristle holder includes a plurality of rows of bristle tufts.

16. The electric toothbrush of claim 1, wherein the head has slots within which the second bristle holder is movably mounted.

17. An electric toothbrush, comprising:
   a handle at a first end of the toothbrush having a motor disposed wherein;
   a head at a second end of the toothbrush, the head having a longitudinal axis, the head having a first bristle holder with a plurality of bristle tufts and a second bristle holder with a plurality of bristle tufts; and
   a rotatable shaft operatively connected to the motor and having a longitudinal axis and a cam, wherein the cam engages a cam contact surface of the second bristle holder to move the second bristle holder in a direction substantially perpendicular to the longitudinal axis of the rotatable shaft and wherein the rotatable shaft engages the first bristle holder to oscillate or rotate the first bristle holder about an axis substantially perpendicular to the longitudinal axis of the rotatable shaft, and wherein the second bristle holder reciprocates in a direction generally parallel with the axis of the first bristle holder.

18. The electric toothbrush of claim 17, wherein a gap is defined between the first bristle holder and the second bristle holder, and the toothbrush further comprises static bristles disposed in the gap.

19. The electric toothbrush of claim 17, wherein the cam is a bend in the rotatable shaft.

20. The electric toothbrush of claim 17, wherein the second bristle holder is disposed between the handle and the first bristle holder and the rotatable shaft passes under the second bristle holder and does not pass under the first bristle holder.

21. The electric toothbrush of claim 17, wherein the first bristle holder is driven by a remote-most end of the rotatable shaft.

22. The electric toothbrush of claim 21, wherein the remote-most end is displaced from the cam.

23. The electric toothbrush of claim 17, wherein the head further comprises a shaft support disposed between the first bristle holder and the second bristle holder.

24. The electric toothbrush of claim 17, wherein a remote-most end of the rotatable shaft is offset from the longitudinal axis of the rotatable shaft and engages a slot in the first bristle holder.

25. The electric toothbrush of claim 17, wherein the cam disengages from the second bristle holder such that during disengagement between the cam and the second bristle holder, the second bristle holder is movable towards the head of the toothbrush.

26. The electric toothbrush of claim 17, wherein the second bristle holder includes a plurality of rows of bristles tufts.

27. The electric toothbrush of claim 17, wherein the head has slots within which the second bristle holder is movably mounted.

28. An electric toothbrush head assembly adapted for coupling to a handle having an electric motor, the head assembly comprising:
   a head having a first end adapted for coupling to the handle, and a second end opposite from the first end, the head having a longitudinal axis, the head having a first bristle holder with a plurality of bristle tufts and a second bristle holder with a plurality of bristle tufts; and
   a rotatable shaft operatively connected to the motor and having a longitudinal axis and a cam, wherein the cam engages a cam contact surface of the second bristle holder to move the second bristle holder in a direction substantially perpendicular to the longitudinal axis of the rotatable shaft and wherein the rotatable shaft engages the first bristle holder to oscillate or rotate the first bristle holder about an axis substantially perpendicular to the longitudinal axis of the rotatable shaft, and wherein the second bristle holder moves in a direction generally parallel with the axis of the first bristle holder.

29. The electric toothbrush of claim 28, wherein a gap is defined between the first bristle holder and the second bristle holder.

30. The electric toothbrush of claim 29, wherein the head further comprises static bristles.

31. The electric toothbrush of claim 30, wherein the static bristles are disposed in the gap.

32. The electric toothbrush of claim 28, wherein the second bristle holder is disposed between the handle and the first bristle holder.

33. The electric toothbrush of claim 28, wherein the cam is a bend in the rotatable shaft.

34. The electric toothbrush of claim 33, wherein the second bristle holder has a cam contact surface for engaging the bend of the rotatable shaft.

35. The electric toothbrush of claim 34, wherein the cam contact surface is located on a bottom surface of the second bristle holder.

36. The electric toothbrush of claim 28, wherein the first bristle holder is driven by a remote-most end of the rotatable shaft.

37. The electric toothbrush of claim 36, wherein the remote-most end is displaced from the cam.

38. The electric toothbrush of claim 37, wherein the head further comprises a shaft support disposed between the first bristle holder and the second bristle holder.

39. The electric toothbrush of claim 36, wherein the remote-most end of the rotatable shaft is offset from a longitudinal axis of the rotatable shaft and engages a slot in the first bristle holder.

40. The electric toothbrush of claim 28, wherein the rotatable shaft passes under the second bristle holder and does not pass under the first bristle holder.

41. The electric toothbrush of claim 28, wherein the second bristle holder includes a plurality of rows of bristle tufts.

42. The electric toothbrush of claim 28, wherein the head has slots within which the second bristle holder is movably mounted.

43. The electric toothbrush of claim 28, wherein the cam disengages from the second bristle holder such that during disengagement between the cam and the second bristle holder, the second bristle holder is movable towards the head of the toothbrush.

* * * * *